(12) United States Patent
Ideker et al.

(10) Patent No.: US 7,522,958 B2
(45) Date of Patent: Apr. 21, 2009

(54) METHODS AND SYSTEMS FOR REDUCING DISCOMFORT FROM CARDIAC DEFIBRILLATION SHOCKS

(75) Inventors: Raymond E. Ideker, Birmingham, AL (US); Gregory P. Walcott, Wilsonville, AL (US)

(73) Assignee: UAB Research Foundation, Birmingham, AL (US)

( * ) Notice: Subject to any disclaimer, the term of this patent is extended or adjusted under 35 U.S.C. 154(b) by 1109 days.

(21) Appl. No.: 10/388,211

(22) Filed: Mar. 13, 2003

(65) Prior Publication Data

US 2006/0155334 A1 Jul. 13, 2006

(51) Int. Cl.
*A61N 1/39* (2006.01)
(52) U.S. Cl. .......................................................... 607/5
(58) Field of Classification Search ................... 607/63, 607/6, 7
See application file for complete search history.

(56) References Cited

U.S. PATENT DOCUMENTS

| | | | |
|---|---|---|---|
| 3,805,795 A | 4/1974 | Denniston et al. | 607/6 |
| 3,825,015 A | 7/1974 | Berkovits | 128/404 |
| 3,995,623 A | 12/1976 | Blake et al. | 128/2.06 E |
| 4,355,646 A | 10/1982 | Kallok et al. | 128/786 |
| 4,365,639 A | 12/1982 | Goldreyer | 128/786 |
| 4,444,195 A | 4/1984 | Gold | 128/642 |
| 4,499,907 A | 2/1985 | Kallok et al. | 128/786 |
| 4,559,946 A | 12/1985 | Mower | 128/419 D |
| 4,567,901 A | 2/1986 | Harris | 128/786 |
| 4,637,397 A | 1/1987 | Jones et al. | 128/419 D |
| 4,643,201 A | 2/1987 | Stokes | 128/786 |
| 4,693,253 A | 9/1987 | Adams | 128/419 D |
| 4,708,145 A | 11/1987 | Tacker, Jr. et al. | 128/419 D |
| 4,800,883 A | 1/1989 | Winstrom | 128/419 D |
| 4,850,357 A | 7/1989 | Bach, Jr. | 128/419 D |
| 4,901,725 A | 2/1990 | Nappholz et al. | 128/419 |
| 4,928,688 A | 5/1990 | Mower | 128/419 |
| 4,996,984 A * | 3/1991 | Sweeney | 607/5 |

(Continued)

FOREIGN PATENT DOCUMENTS

EP     0095726 B1    2/1988

(Continued)

OTHER PUBLICATIONS

Qin et al., "Impact of Myocardial Ischemia and Reperfusion on Ventricular Defibrillation Patterns, Energy Requirements, and Detection of Recovery", American Heart Association, Inc., 2002:105:2537, May 6, 2002.

(Continued)

*Primary Examiner*—Carl H. Layno
*Assistant Examiner*—Jon-Eric C. Morales
(74) *Attorney, Agent, or Firm*—Myers Sigel Sibley & Sajovec

(57) ABSTRACT

Methods, systems and computer program products for combining atrial defibrillation treatment techniques include techniques for reducing the discomfort associated with defibrillation and/or reducing the defibrillation threshold. Techniques include timing the defibrillation shock to reduce discomfort based on a sensed signal, giving the shock relatively early during atrial fibrillation, therapeutic drugs, administering more than one shock in succession, pacing the heart before, after, or during the defibrillation shock or shocks, and placing the shock electrodes in locations that may reduce discomfort.

12 Claims, 8 Drawing Sheets

U.S. PATENT DOCUMENTS

| | | | |
|---|---|---|---|
| 5,107,834 A | 4/1992 | Ideker et al. | 128/419 D |
| 5,161,528 A | 11/1992 | Sweeney | 128/419 |
| 5,165,403 A | 11/1992 | Mehra | 128/419 |
| 5,184,616 A | 2/1993 | Weiss | 128/419 |
| 5,201,808 A | 4/1993 | Steinhaus et al. | 128/419 |
| 5,209,229 A | 5/1993 | Gilli | 128/419 |
| 5,224,476 A | 7/1993 | Ideker et al. | 128/419 D |
| 5,230,337 A | 7/1993 | Dahl et al. | 607/5 |
| 5,235,977 A | 8/1993 | Hirschberg et al. | 607/5 |
| 5,235,978 A | 8/1993 | Hirschberg et al. | 607/5 |
| 5,251,624 A | 10/1993 | Bocek et al. | 607/6 |
| 5,267,559 A | 12/1993 | Jin et al. | 128/419 D |
| 5,269,298 A | 12/1993 | Adams et al. | 128/419 D |
| 5,269,319 A | 12/1993 | Schulte et al. | 128/786 |
| 5,282,836 A | 2/1994 | Kreyenhagen et al. | 607/4 |
| 5,292,338 A | 3/1994 | Bardy | 607/5 |
| 5,303,702 A | 4/1994 | Bonnet et al. | 607/20 |
| 5,304,139 A | 4/1994 | Adams et al. | 607/122 |
| 5,304,218 A | 4/1994 | Alferness | 607/122 |
| 5,312,444 A | 5/1994 | Bocek et al. | 607/5 |
| 5,313,953 A | 5/1994 | Yomtov et al. | 600/508 |
| 5,314,430 A | 5/1994 | Bardy | 607/5 |
| 5,324,309 A | 6/1994 | Kallok | 607/5 |
| 5,331,966 A | 7/1994 | Bennett et al. | 128/696 |
| 5,332,400 A | 7/1994 | Alferness | 607/5 |
| 5,344,430 A | 9/1994 | Berg et al. | 607/8 |
| 5,348,021 A | 9/1994 | Adams et al. | 128/708 |
| 5,350,402 A | 9/1994 | Infinger et al. | 607/5 |
| 5,366,485 A | 11/1994 | Kroll et al. | 607/5 |
| 5,366,486 A | 11/1994 | Zipes et al. | 607/5 |
| 5,387,233 A | 2/1995 | Alferness et al. | 607/126 |
| 5,395,373 A | 3/1995 | Ayers | 607/8 |
| 5,403,351 A | 4/1995 | Saksena | 607/4 |
| 5,403,354 A | 4/1995 | Adams et al. | 607/5 |
| 5,405,375 A | 4/1995 | Ayers et al. | 607/122 |
| 5,411,527 A * | 5/1995 | Alt | 607/5 |
| 5,423,772 A | 6/1995 | Lurie et al. | 607/282 |
| 5,431,681 A | 7/1995 | Helland | 607/4 |
| 5,431,682 A | 7/1995 | Hedberg | 607/5 |
| 5,431,683 A | 7/1995 | Bowald et al. | 607/5 |
| 5,433,729 A | 7/1995 | Adams et al. | 607/5 |
| 5,433,730 A | 7/1995 | Alt | 607/5 |
| 5,441,519 A | 8/1995 | Sears | 607/5 |
| 5,443,491 A | 8/1995 | Snichelotto | 607/122 |
| 5,447,519 A | 9/1995 | Peterson | 607/5 |
| 5,456,706 A | 10/1995 | Pless et al. | 607/122 |
| 5,464,429 A | 11/1995 | Hedberg et al. | 607/4 |
| 5,464,432 A | 11/1995 | Infinger et al. | 607/5 |
| 5,470,348 A | 11/1995 | Neubauer et al. | 607/68 |
| 5,476,498 A | 12/1995 | Ayers | 607/122 |
| 5,476,499 A | 12/1995 | Hirschberg | 607/123 |
| 5,486,199 A | 1/1996 | Kim et al. | 607/5 |
| 5,487,753 A | 1/1996 | MacCarter et al. | 607/17 |
| 5,489,293 A | 2/1996 | Pless et al. | 607/5 |
| 5,522,853 A | 6/1996 | Kroll | 607/5 |
| 5,531,764 A | 7/1996 | Adams et al. | 607/5 |
| 5,554,176 A | 9/1996 | Maddison et al. | 607/9 |
| 5,560,369 A | 10/1996 | McClure et al. | 128/704 |
| 5,578,064 A | 11/1996 | Prutchi | 607/19 |
| 5,584,865 A | 12/1996 | Hirschberg et al. | 607/5 |
| 5,601,608 A | 2/1997 | Mouchawar | 607/5 |
| 5,609,621 A | 3/1997 | Bonner | 607/122 |
| 5,620,471 A | 4/1997 | Duncan | 607/14 |
| 5,662,689 A * | 9/1997 | Elsberry et al. | 607/5 |
| 5,683,429 A | 11/1997 | Mehra | 602/14 |
| 5,697,953 A | 12/1997 | Kroll et al. | 607/5 |
| 5,718,718 A | 2/1998 | Kroll et al. | 607/5 |
| 5,800,469 A | 9/1998 | Nappholz | 607/18 |
| 5,800,470 A | 9/1998 | Stein et al. | 607/20 |
| 5,851,220 A | 12/1998 | Murphy | 607/5 |
| 5,861,012 A | 1/1999 | Stroebel | 607/28 |
| 5,954,752 A * | 9/1999 | Mongeon et al. | 607/6 |
| 5,978,704 A | 11/1999 | Ideker et al. | 607/5 |
| 5,978,705 A | 11/1999 | KenKnight et al. | 607/5 |
| 5,987,354 A | 11/1999 | Cooper et al. | 607/5 |
| 6,002,962 A | 12/1999 | Huang et al. | 607/5 |
| 6,006,131 A | 12/1999 | Cooper et al. | 607/5 |
| 6,122,553 A | 9/2000 | Ideker et al. | 607/122 |
| 6,148,230 A | 11/2000 | KenKnight | 600/516 |
| 6,205,357 B1 | 3/2001 | Ideker et al. | 607/14 |
| 6,263,241 B1 | 7/2001 | Rosborough et al. | 607/5 |
| 6,266,563 B1 * | 7/2001 | KenKnight et al. | 607/5 |
| 6,275,730 B1 | 8/2001 | KenKnight et al. | 607/5 |
| 6,285,907 B1 | 9/2001 | Kramer et al. | 607/9 |
| 6,327,500 B1 * | 12/2001 | Cooper et al. | 607/5 |
| 2003/0018361 A1 | 1/2003 | Herleikson | 607/5 |
| 2004/0049117 A1 | 3/2004 | Ideker et al. | 600/510 |

FOREIGN PATENT DOCUMENTS

| | | |
|---|---|---|
| EP | 0472 411 A1 | 2/1992 |
| EP | 0554 208 A2 | 8/1993 |
| EP | 0601340 A1 | 6/1994 |
| EP | 0653223 A2 | 10/1994 |
| EP | 0804938 A2 | 11/1997 |
| WO | WO96/23546 | 8/1996 |
| WO | WO 97/01373 | 1/1997 |
| WO | WO99/65561 | 12/1999 |

OTHER PUBLICATIONS

Walcott et al., "Choosing the Optimal Monophasic and Biphasic Waveforms for Ventricular Defibrillation", Journal of Cardiovascular Electrophysiology, vol. 6, No. 9, pp. 737-750, Sep. 1995.

White et al., "Predicting the Relative Efficacy of Shock Waveforms for Transthoracic Defibrillation in Dogs", 34:3, Annals of Emergency Medicine, pp. 309-320, Sep. 1999.

Allessie et al., "Regional control of atrial fibrillation by rapid pacing in concious dogs," *Circulation* 1991;84:1689-1697.

Capucci et al., "Capture window in human atrial fibrillation: evidence of an excitable gap," *J Cardiovasc Electrophysiol* 1999;10:319-327.

Cooper et al., "Internal Cardioversion of Atrial Fibrillation in Sheep," Atrial Fibrillation: Mechanisms and Therapeutic Strategies, pp. 325-332 (1994).

Cooper et al., "Internal Cardioversion of Atrial Fibrillation in Sheep," Circulation, vol. 87, No. 5, May 1993, pp. 1673-1685.

Daoud et al. "Response of Type I atrial fibrillation to atrial pacing in humans," Circulation 1996;94:1036-1040.

Feeser et al., "Strength-Duration and Probability of Success Curves for Defibrillation with Biphasic Waveforms," *Circulation*, vol. 82, No. 6, Dec. 1990, pp. 2128-2141.

García-Calvo et al., "The effects of selective stellate ganglion manipulation on ventricular refractoriness and excitability," PACE, 1992;15:1492-1503.

Huang et al., "Evolution of the organization of epicardial activation patterns during ventricular fibrillation," J Cardiovasc Electrophysiol, 1998;9:1291-1304.

KenKnight et al., "Regional capture of fibrillating ventricular myocardium: Evidence of an excitable gap," Circ Res 1995;77:849-855.

Kirchhof et al., "Regional entrainment of atrial fibrillation studied by high-resolution mapping in open-chest dogs," Circulation 1993;88:736-749.

Knisley et al., "Line stimulation parallel to myofibers enhances regional uniformity of transmembrane voltage changes in rabbit hearts," Circ Res 1997;81:229-241.

Kroll, Mark W., "A Minimal Model of the Monophasic Defibrillation Pulse," PACE, vol. 16, Apr. 1993, Part I, pp. 769-777.

Lammers, W. J.E.P. et al., *The use of fibrillation cycle length to determine spatial dispersion in electrophysiological properties and to characterize the underlying mechanism of fibrillation*, New Trends in Arrhythmias, vol. 11, N. 1, Jan.-Mar. 1986, pp. 109-112.

Laxer, Cary et al., *The Use of Computer Animation of Mapped Cardiac Potentials in Studying Electrical Conduction Properties of Arrhythmias*, IEEE, 1991, pp. 23-26.

Lewalter et al., "The Low Intensity Treadmill Exercise" Protocol for Appropriate Rate Adaptive Programming of Minute Ventilation Controlled Pacemakers, PACE, 18:1374-1387 (Jul. 1995).

Lok et al.; "Clinical Shock Tolerability and Effect of Different Right Atrial Electrode Locations on Efficacy of Low Energy Human Transvenous Atrial Defibrillation Using an Implantable Lead System", *JACC* 30:5 1324-1330 (1997).

Lüderitz et al., "Nonpharmacologic Strategies for Treating Atrial Fibrillation," The American Journal of Cardiology, vol. 77, Jan. 25, 1996, pp. 45A-52A.

Neri et al.; "Internal Cardioversion of Chronic Atrial Fibrillation in Patients", *PACE* 20 2237-2242 (1997).

Opthof et al., "Dispersion of refracteries in canine ventricular myocardium: Effects of sympathetic stimulation," Circ Res 1991;68:1204-1215.

Prof. Dr. med. Eckhard Alt; "Letters to the Editor", *PACE* 21 633-634 (1998).

Province et al., "Effect of pulse train amplitude and waveform on ability to entrain fibrillating rabbit ventricle with epicardial pacing," PACE, 22:A66 (1999) (Abstract).

Qin, Hao et al., "Recurrence Patterns After Failed Defibrillation of Spontaneous Ventricular Fibrillation During Acute Ischemia," Supplement to Journal of the American College of Cardiology, p. 3, Mar. 6, 2002, vol. 39, No. 5 Supplement A.

Qin, Hao et al., "Difibrillation Efficacy for Spontaneous and electrically-Induced Ventricular Fibrillation During Acute Ischemia," Supplement to Circulation Journal of the Americam Heart Association, #2125, 2000.

Qin, Hao et al., "Impact of Myocardial Ischemia and Reperfusion on Ventricular Defibrillation Patterns, Energy Requirements, and Detection of Recovery," (Circulation 2002;105:2537) Published online before print May 6, 2002, 10.1161/01.CIR.0000016702.86180.F6.

Rogers et al., "A quantitative framework for analyzing epicardial activation patterns during ventricular fibrillation," Ann Biomed Eng 1997;25:749-760.

Rogers et al., "Recurrent wavefront morphologies: a method for quantifying the complexity of epicardial activation patterns," Ann Biomed Eng 1997;25:761-768.

Rollins et al., "Macintosh based programmable cardiac stimulatr," J Am Coll Cardiol, 15:261A (1990) Abstract.

Vander et al., *"Human Physiology—The Mechanisms of Body Functio,"* pp. 230-236, Jan. 1985.

Wharton et al., "Cardiac potential and potential gradient fields generated by single, combined, and sequential shocks during ventricular defibrillation," Circulation 1992;85:1510-1523.

Wolf, P. D. et al., *A 528 Channel System for the Acquisition and Display of Defibrillation and Electrocardiographic Potentials*, IEEE, 1993, pp. 125-128.

Wright et al., "Cardiac Rhythm Management Laboratory: In Vivo Study Protocol, Internal Atrial Defibrillation in Sheep Using Sequential Biphasic Waveforms," CRM Laboratory, University of Alabama—Birmingham Medical Center, Oct. 1995.

PCT International Search Report, International Application No. PCT/US01/47195 dated Jul. 23, 2002.

Office Action from U.S. Appl. No. 10/238,342, mailed Oct. 3, 2005.
Office Action from U.S. Appl. No. 10/238,342, mailed Nov. 15, 2005.
Office Action from U.S. Appl. No. 10/238,342, mailed Apr. 24, 2006.
Office Action from U.S. Appl. No. 10/238,342, mailed Jul. 13, 2006.

* cited by examiner

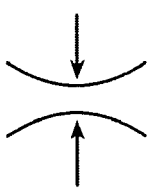
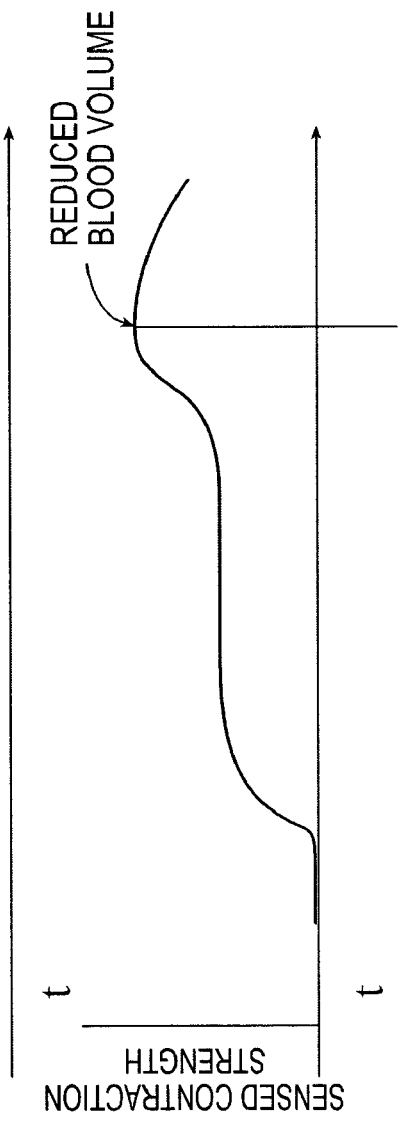
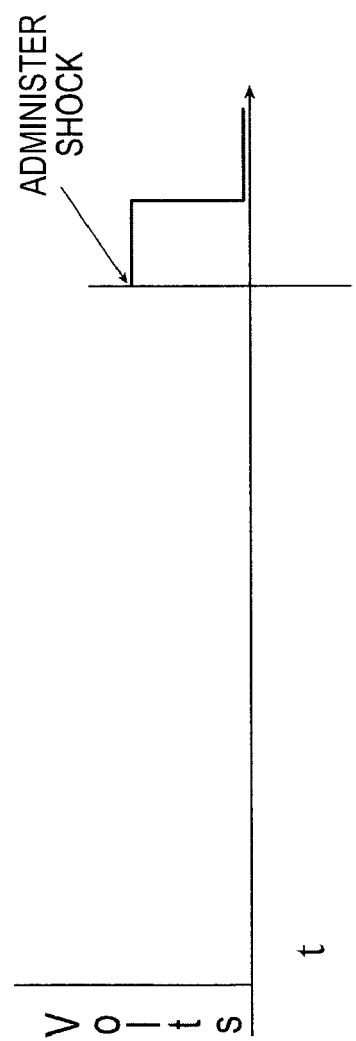
FIG. 2A
FIG. 2B
FIG. 2C

METHODS AND SYSTEMS FOR REDUCING DISCOMFORT FROM CARDIAC DEFIBRILLATION SHOCKS

FIELD OF THE INVENTION

The present invention concerns methods and systems that may reduce patient discomfort associated with therapeutic cardiac shocks.

BACKGROUND OF THE INVENTION

Atrial fibrillation is one of the most common cardiac arrhythmia. Atrial fibrillation is a debilitating disease that afflicts 20 million people worldwide. Health consequences associated with atrial fibrillation include decreased cardiac output, less regular ventricular rhythm, the formation of blood clots in the atrial appendages, and an increased incidence of stroke. While some drugs are available for the treatment of atrial fibrillation, they have a number of side effects which reduce their therapeutic utility. The use of atrial counter shocks remains one of the primary treatments for atrial fibrillation.

Anatomically, the heart includes a fibrous skeleton, valves, the trunks of the aorta, the pulmonary artery, and the muscle masses of the cardiac chambers (i.e., right and left atria and right and left ventricles). The driving force for the flow of blood in the heart comes from the active contraction of the cardiac muscle. This contraction can be detected as an electrical signal.

The beginning of a cardiac cycle is initiated by a P wave, which is normally a small positive wave in the body surface electrocardiogram. The P wave induces depolarization of the atria of the heart. The P wave is followed by a cardiac cycle portion which is substantially constant with a time interval on the order of 120 milliseconds ("ms").

The "QRS complex" of the cardiac cycle occurs after the substantially constant portion. The dominating feature of the QRS complex is the R wave which is a rapid positive deflection. The R wave generally has an amplitude greater than any other wave of the cardiac cycle, and has a spiked shape of relatively short duration with a sharp rise, a peak amplitude, and a sharp decline. The R wave is the depolarization of the ventricles and therefore, as used herein, the term "ventricle activations" denotes R waves of the cardiac cycle. The QRS complex is completed by the S wave, which is typically a small negative deflection that then returns the cardiac signal to baseline.

Following the S wave, the T wave occurs after a delay of about 250 ms. The T wave is relatively long in duration (e.g., about 150 ms). The cardiac cycle between the S wave and the T wave is commonly referred to as the ST segment. The T wave is a sensitive part of the cardiac cycle, during which an atrial defibrillation shock is to be avoided, in order to reduce the possibility of induced (and often fatal) ventricular fibrillation. The next cardiac cycle begins with the next P wave. The typical duration of a complete cardiac cycle is on the order of about 800 ms.

Unlike patients afflicted with ventricular fibrillation, patients afflicted with atrial fibrillation are conscious. The pain associated with the administration of the defibrillation shock can be severe, and there is a need to reduce the pain to the patient being treated while maintaining clinical efficacy of the defibrillation shock. Other fibrillation-based conditions in which pain may be experienced by the patient include shock treatment of hemodynamically stable ventricular tachycardia.

SUMMARY OF THE INVENTION

Embodiments of the present invention employ operations that can reduce fibrillation shock discomfort and/or promote clinical efficacy of therapeutic shocks administered to a subject that is conscious. Particular embodiments are directed at administering combinations of therapies or shock types during an episodic treatment cycle.

Examples of treatment techniques that may be combined in a single episodic treatment include 1) optimizing the shock waveform so that it is less painful, by using a waveform that requires less shock energy, voltage, and/or current and/or using a shock waveform that is intrinsically less painful, 2) timing the defibrillation shock to minimize discomfort based on a sensed signal, such as an electrode recording of the atrial fibrillation electrical complex, 3) giving the shock relatively early during onset of atrial fibrillation, 4) administering therapeutic drugs either by the defibrillator, by the patient, or by the healthcare provider, including drugs that lower the defibrillation threshold as well as drugs that decrease the sensed discomfort associated with the shock, 5) administering more than one shock in succession to lower the defibrillation threshold or to decrease the sensed discomfort associated with the shocks, 6) pacing the heart before, after, or during the defibrillation shock or shocks 7) delivering shocks from electrode locations that may reduce discomfort, for example, by delivering one shock, sequential shocks, or overlapping shocks from three or more electrodes. Atrial defibrillators may be configured to perform any combination of one, two or more of the above techniques.

In some embodiments, a time during the cardiac cycle at which atrial blood volume is reduced is determined, and a defibrillation shock is delivered to the heart at the time at which atrial blood volume is reduced. The cardiac cycle may be detected to determine the time at which atrial blood volume is reduced and/or a preparatory shock to the atria of the heart may be delivered to contract the atria followed by a defibrillation shock during the contraction of the atria caused by the preparatory shock.

In other embodiments, a system for treating arrhythmia includes an arrhythmia detector configured to determine if a cardiac arrhythmia is occurring and to detect the cardiac cycle from electrical activity sensed from the heart of a subject. A controller is operatively associated with the detector, and a shock generator is operatively associated with the controller. The controller is configured to direct the shock generator to deliver a defibrillation shock to one or more electrodes placed in operative association with the heart at a time during the cardiac cycle at which atrial blood volume is reduced.

In further embodiments, a biphasic waveform defibrillation shock is delivered to the cardiac region. The biphasic waveform has a first ascending phase and a second phase of opposite polarity. The first ascending phase maintains an effective voltage greater than about 50 to about 80% of the peak voltage for a duration greater than about 0.5 to about 1.0 ms.

In still further embodiments, an arrhythmia detector is configured to determine if a cardiac arrhythmia is occurring from electrical activity sensed from the heart of a subject. A controller is operatively associated with the detector, and a shock generator is operatively associated with the controller. The controller is configured to direct the shock generator to deliver a biphasic waveform shock through one or more defibrillation electrodes placed in operative association with the heart. The biphasic waveform has a first ascending phase and a second phase of opposite polarity. The first ascending phase maintains an effective voltage greater than about 50 to about 80% of the peak voltage for a duration greater than about 0.5 to about 1.0 ms.

BRIEF DESCRIPTION OF THE DRAWINGS

FIGS. 2A, 2B, and 2C are graphs comparing the contraction of the atria (FIG. 2A), the sensed contraction strength (FIG. 2B), and the time at which the shock is delivered (FIG. 2C).

DETAILED DESCRIPTION OF EMBODIMENTS OF THE INVENTION

Figure 1:
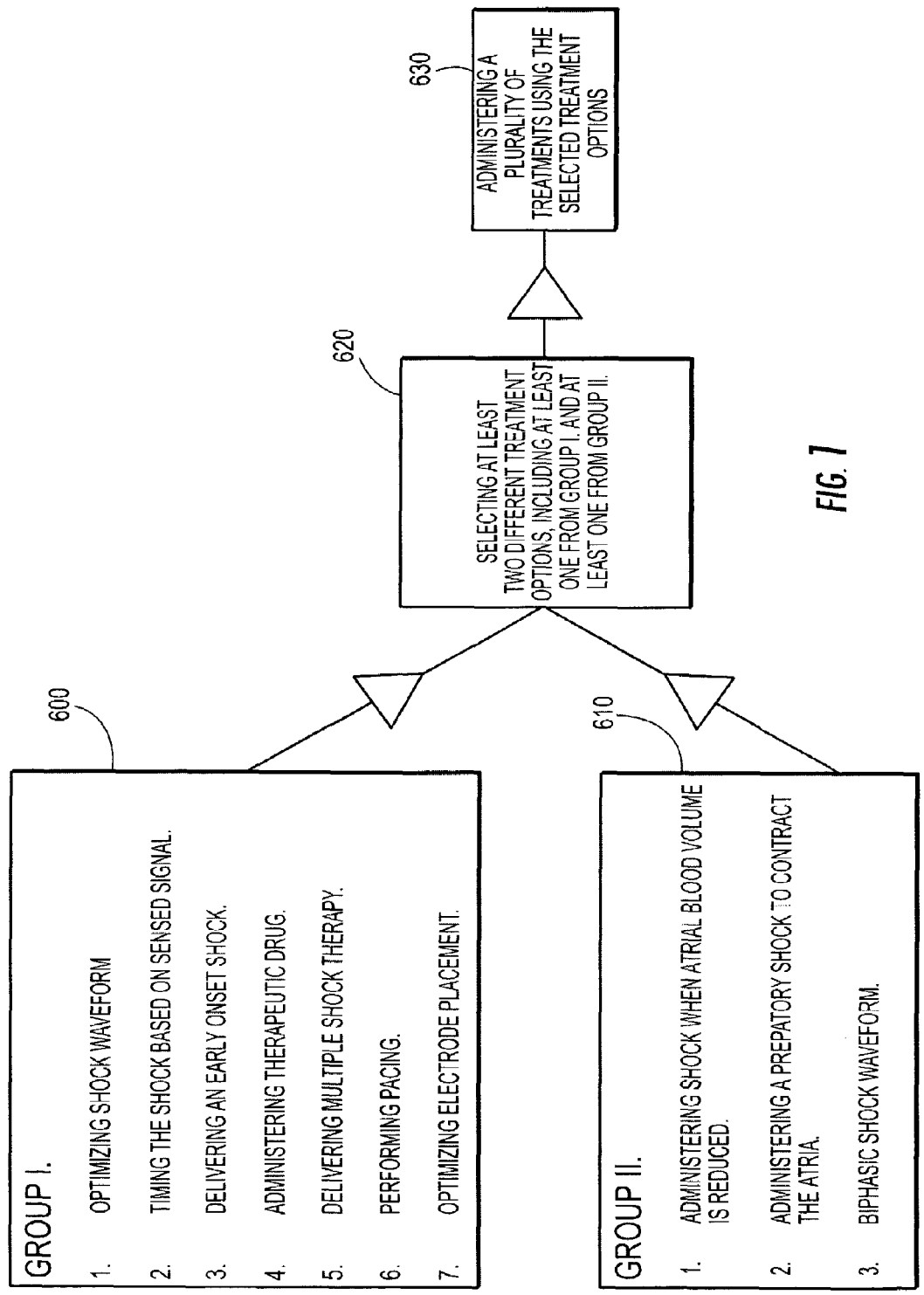
FIG. 1 is a block diagram illustrating operations that can be carried out according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain regions, components, features or layers may be exaggerated for clarity. Broken lines where used indicate optional features, components or operations unless stated otherwise.

The flowcharts and block diagrams of certain of the figures herein illustrate the architecture, functionality, and operation of possible implementations for reducing patient discomfort according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved. In addition, some functions noted in the blocks may be combined or separated.

The present invention may be used to treat all forms of cardiac tachyarrhythmias, including atrial and ventricular fibrillation, with defibrillation (including cardioversion) shocks or pulses. Examples include treatment of polymorphic ventricular tachycardia, monomorphic ventricular tachycardia, ventricular fibrillation, atrial flutter, and atrial fibrillation. The present invention is particularly useful for treating cardioversion or defibrillation of atrial fibrillation, flutter or hemodynamically stable ventricular tachycardia and other conditions in which patient discomfort may be a therapeutic consideration and/or barrier to the clinical acceptance of treatment.

Typically, the issue of shock discomfort is not as great for ventricular fibrillation because ventricular fibrillation is usually immediately life-threatening and often renders the patient unconscious. However, in cases of cardioversion or defibrillation of atrial fibrillation, flutter or hemodynamically stable ventricular tachyardia, the rhythms are not usually immediately life-threatening, and many patients experience these rhythms with relatively frequent occurrences and are often conscious when they occur. Therefore, patient acceptance of therapy involving implantable device-based cardioversion/defibrillation, external defibrillation, and cardioversion on an unsedated patient may be limited by patient discomfort associated with defibrillation shocks.

Embodiments of the present invention include combining two or more techniques that can reduce discomfort and/or the defibrillation shock threshold during atrial defibrillation.

In the past, a number of techniques have been proposed to lower the defibrillation threshold, that is, the shock strength required for atrial defibrillation. A lower defibrillation shock strength may decrease the discomfort associated with the shock. As used herein, a "shock profile" is a group of parameters associated with a defibrillation shock or shock sequence, including voltage, waveforms (shapes), energy and electrical current parameters. Other techniques propose decreasing the level of discomfort associated with a shock without necessarily lowering the defibrillation threshold, for example, by selecting a shock profile that is intrinsically less painful. Shock profiles for reducing discomfort and/or reducing the defibrillation threshold may be selected using the techniques and devices described in co-owned, co-pending U.S. application Ser. No. 10/234,624, which is hereby incorporated by reference in its entirety.

Other techniques include timing the defibrillation shock to reduce discomfort based on a sensed signal associated with the cardiac cycle or an indication of the initiation of an atrial fibrillation, such as electrode recording of the atrial fibrillation electrical complex. Giving the shock relatively early during atrial fibrillation may also reduce discomfort because the atrial defibrillation threshold may be lower soon after atrial fibrillation begins and increase with time. See, e.g., U.S. Pat. No. 6,205,357. Certain therapeutic drugs may be administered, either by the defibrillator, by the patient or by a healthcare provider to either lower the defibrillation threshold and/or to reduce the sensed discomfort associated with the shock. See, e.g., patent application Ser. No. 10/071,269. Administering more than one shock in succession may also lower the defibrillation threshold and/or decrease the sensed discomfort associated with the shock. See, e.g., U.S. Pat. Nos. 5,978,704; 5,987,354; 6,327,500; and co-pending, co-owned patent application Ser. No. 10/087,340. Pacing the heart before, after, or during the defibrillation shock or shocks may also lower the defibrillation threshold and/or decrease the sensed discomfort associated with the shock. See, e.g., U.S. Pat. No. 6,266,563; (co-pending, co-owned) patent application Ser. Nos. 10/238,342; 10/238,340; 10/238,343. Another technique for reducing discomfort includes administering a shock, sequence of shocks, or overlapping shocks from shock electrodes selectively placed in locations that may reduce discomfort. See, e.g., U.S. Pat. Nos. 5,978,704; 5,987,354; 6,327,500 and (co-pending, co-owned) patent application Ser. Nos. 09/827,535 and 10/087,340. For example, one shock, sequential shocks or overlapping shocks may be delivered from three or more electrodes to reduce discomfort and/ or the defibrillation threshold. The above patents and patent applications are hereby incorporated by reference in their entirety.

Without wishing to be bound by only one theory, it is believed that discomfort levels may be further decreased and/or lower defibrillation thresholds may be achieved when combination therapies employing two or more techniques are used for lowering the discomfort associated with defibrillation and/or lowering the defibrillation threshold.

FIG. 1 is a diagram illustrating the selection of various treatments according to embodiments of the invention. Group I (Block 600) includes seven techniques for lowering the discomfort associated with defibrillation and/or for lowering the defibrillation threshold. Group I includes 1) optimizing the shock waveform, 2) timing the delivery of the shock based on a sensed signal (e.g., the atrial fibrillation electrical complex), 3) delivering an early onset shock, that is, soon after the onset of defibrillation, 4) administering a therapeutic drug, 5) delivering multiple shock therapy, 6) performing pacing, and 7) optimizing electrode placements. Other techniques known to those of skill in the art may be used. In the example shown, Group II (Block 610) includes three techniques: 1) administering a shock at a time when atrial blood volume is reduced, 2) administering a prepatory shock to contract the atria prior to the defibrillation shock, and 3) administering a biphasic waveform defibrillation shock. However, any selection of techniques may be used and the two groups may be the same or different. At Block 620, at least two treatment options are selected: at least one technique from Group 1 (Block 600) and at least one technique from Group II (Block 610). At Block 630, a plurality of treatments are administered using the selected treatment options.

Shock Sequences and Timing.

Certain treatment techniques may decrease discomfort and/or the defibrillation threshold by reducing the amount of blood in the atria during the delivery of the defibrillation shock. It is believed that timing the shock during a period where there is a decreased volume of blood in the ventricles may decrease the defibrillation threshold or strength of the shock needed for efficacious ventricular defibrillation. Timing the shock delivery during periods where there is decreased blood in the ventricular cavities may decrease the defibrillation threshold by 1) decreasing the amount of current shunting through the highly conductive blood pool and/or 2) decreasing cardiac dimensions, which consequently decreases the distance the current has to flow in the far reaches of the myocardium and may increase the current density in these regions.

Without wishing to be bound by any particular theory, the same theory may apply to the atria. That is, if the amount of blood in the atria at the time the shock is given is decreased, the threshold used to efficaciously halt atrial fibrillation may be lowered. Administering a small preparatory shock, for example, less than about 100V, to the atria to cause it to slightly contract even though it is fibrillating may lower the amount of blood in the atria. A second, typically larger defibrillating shock may be administered at a time when the atria are contracted. Alternatively, or in addition to the preparatory shock, a defibrillation shock may be timed based on the ventricular cardiac cycle. After the end of the ventricular systole, the mitral and tricuspid valves open and blood flows from the atria into the ventricles during the ventricular diastole. The atrial defibrillation shock may be timed to be given at the time in the ventricular diastole that the atrial blood volume is reduced. For example, electrodes can be placed in the right atrial appendage and the coronary sinus, the superior vena cava, and/or the ventricular apex. FIGS. 2A, 2B, and 2C are graphs comparing the contraction of the atria (FIG. 2A), the sensed contraction strength (FIG. 2B), and the time at which the shock is delivered (FIG. 2C). Although the shock shown in FIG. 2C is a square wave, any waveform can be used, including waveforms discussed herein. The sensed contraction strength shown in FIG. 2B may be obtained from electrical signals sensed in the cardiac region.

The shock sequence can include delivering a first shock to the atria of the heart of a subject experiencing arrhythmia. It is believed that the first shock can cause the atria to contract, thus reducing the amount of blood in the atria for a time period subsequent to the shock. A second shock can then be delivered during contraction of the atria. The first shock has a strength less than the second shock. For example, the first shock can be between about 5 volts and about 100 volts, and is preferably about 25 volts. The second shock strength can be between about 10 volts and about 200 volts, and is preferably about 50 volts. The time between the shocks can be between about 50 ms and about 500 ms.

In further embodiments, the defibrillation shock is delivered at a time during the cardiac cycle at which blood in the atria is reduced. The ventricular cardiac cycle can be detected, for example, by electrodes or sensors placed to detect electrical signals from the heart. A time during the cardiac cycle at which atrial blood volume is reduced may be determined, for example, when the atria is contracted. The atria may be contracted as a result of a preparatory shock or during the natural cardiac cycle. Blood pressure measurements may also be used to determine a time at which atrial blood volume is reduced. An impedance or conductance catheter can also be used to estimate ventricular volume. Impedance/conductance catheters are discussed in co-pending, co-owned application Ser. No. 10/210,587, the disclosure of which is hereby incorporated by reference in its entirety. The defibrillation shock can be delivered to the heart at the time at which atrial blood volume is reduced. In some embodiments, a preparatory shock is delivered to the atria of the heart of a subject experiencing arrhythmia, for example, to decrease the amount of blood in the atria. A second defibrillation shock can be delivered to the atria at a time during contraction of the atria when there is reduced blood volume.

Another technique for reducing discomfort associated with atrial defibrillation includes timing a series of defibrillation shocks based on the fibrillation cycle length. Certain timing techniques based on the fibrillation cycle length are disclosed in U.S. Pat. No. 5,161,528 to Sweeney, which is hereby incorporated by reference in its entirety. Although the propagation of depolarized waveforms through the myocardium along re-entrant pathways is complex, individual tissue sections are activated with a relatively consistent cyclical timing. The fibrillation cycle length is generally determined by the average time required for a wavefront to complete a re-entrant circuit.

Without wishing to be bound by theory, it is believed that administering a pair of shocks that are spaced apart by about 80% to about 90% of the fibrillation cycle length may more efficiently defibrillate the heart, requiring smaller shock strength and potentially less discomfort. The fibrillation cycle may vary spatially within the heart. For example, the fibrillation cycle can be faster in the right atria. The fibrillation cycle may be detected by an electrode in the coronary sinus proximate the right atria, or in a location that is not proximate to the atria. Preferably, the second shock is spaced apart from the first shock by about 85% of the fibrillation cycle length. Subsequent defibrillation shocks can also be delivered. For example, after the first pair of shocks, subsequent defibrillation shocks may be spaced apart by the time of an entire fibrillation cycle length. This spacing can ensure that each shock is administered at approximately the same point with respect to the fibrillation cycle. That is, the defibrillation shocks administered after the first pair of shocks are preferably not spaced apart by a fraction of the fibrillation cycle length, but rather the entire cycle length such that the shocks administered after the first pair of shocks are administered at approximately the same point of the fibrillation cycle. The second defibrillation shock of the first pair of shocks is delivered at a point between about 80% to about 90% of the fibrillation cycle length. By delaying a third defibrillation shock by the entire length of the fibrillation cycle after the second shock, the third defibrillation shock can also be delivered at a point between about 80% to about 90% of the fibrillation cycle length with respect to a subsequent fibrillation cycle. However, the time between the second and third shocks and any subsequent shocks is between about 90% to about 110% of the fibrillation cycle length.

In some embodiments, the shocks can be between about 5 and about 100 volts. The fibrillation cycle length can be determined various methods, including conventional methods. In certain embodiments, the fibrillation cycle can be detected by sensing electrical activity at electrodes placed around the heart.

Waveforms.

Any suitable waveform may be used to carry out the present invention, including both monophasic, biphasic and triphasic waveforms. Various amplitudes, polarities, and durations of waveforms may be used, as will be apparent to those skilled in the art. Although any suitable waveform can be used for defibrillation, some treatment techniques may decrease discomfort and/or lower the defibrillation threshold by using a biphasic waveform.

Figure 3A:
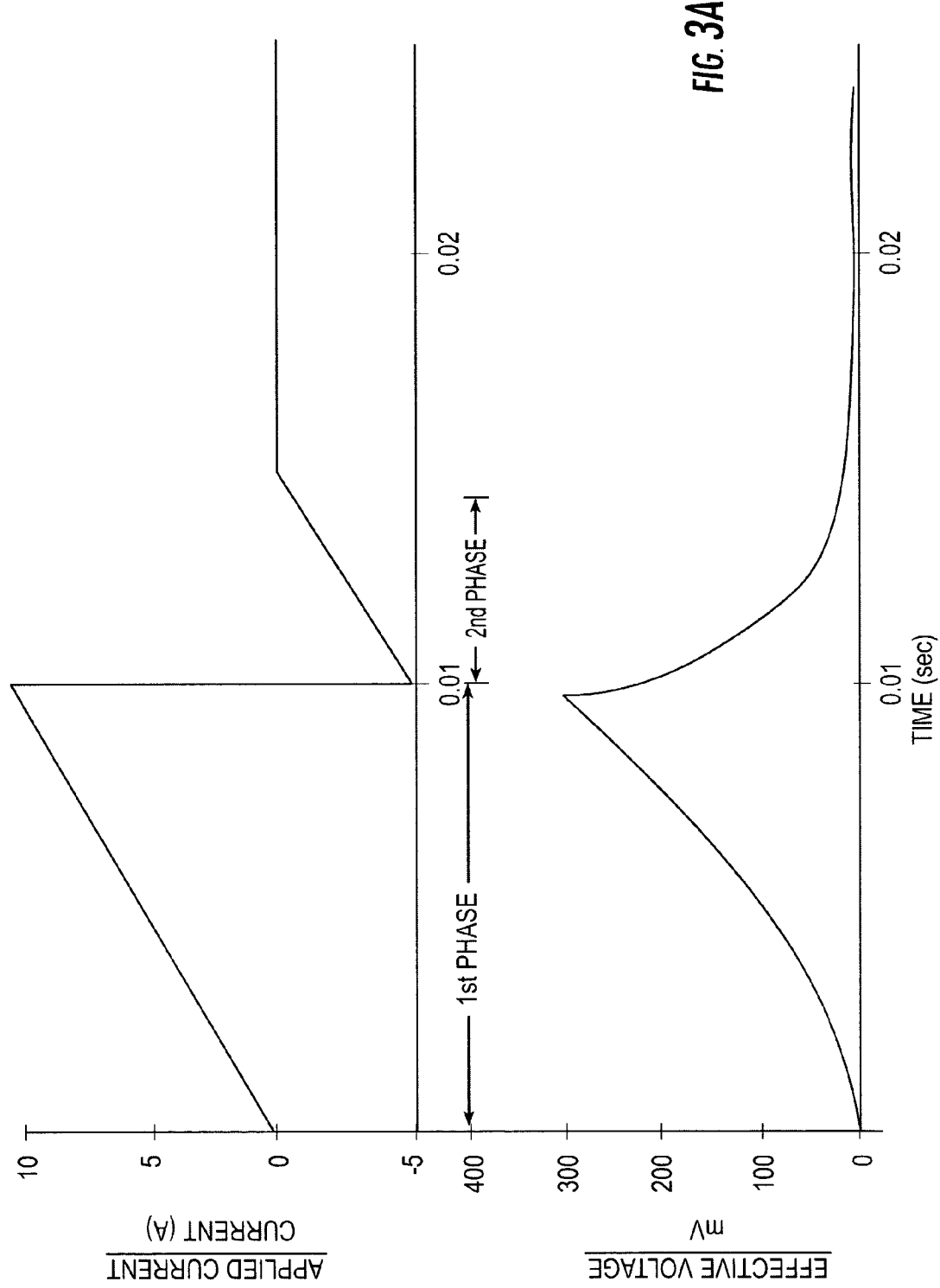
FIGS. 3a and 3b are graphs of current (ampere) versus time (seconds) illustrating biphasic waveforms and their respective effective voltages that may be used to carry out atrial or ventricular defibrillation in accordance with embodiments of the present invention.
Figure 3B:
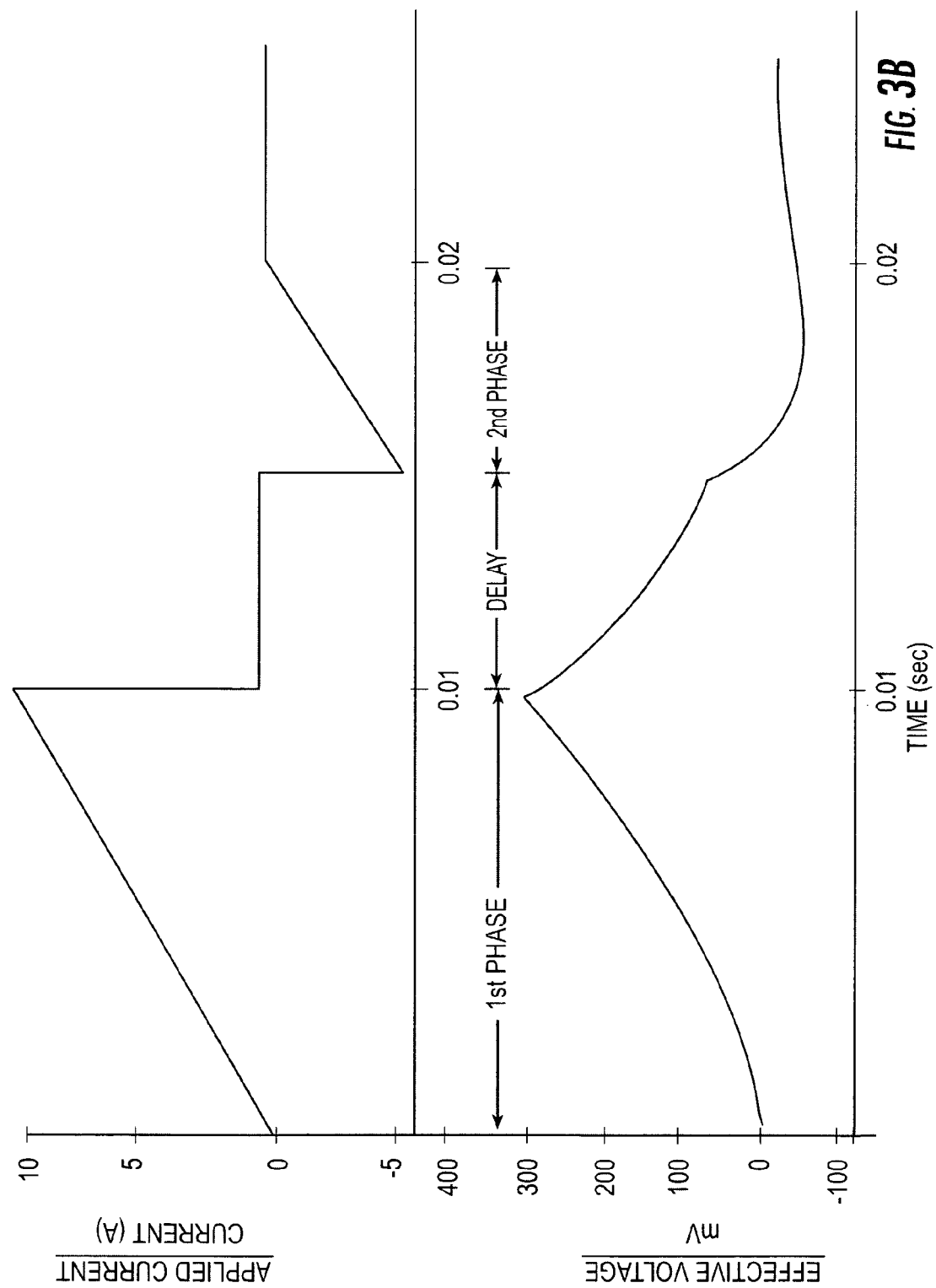

Examples of suitable biphasic waveforms and the resulting effective voltages are shown in FIGS. 3a and 3b.

Examples of suitable biphasic waveforms include biphasic waveforms having a first ascending phase and a second phase of opposite polarity. Short second phases, for example, between 0.5 and 1.0 ms, may decrease the defibrillation threshold. Examples of suitable first phases can include a truncated exponential decreasing waveform, an ascending linear waveform, or a truncated exponential increasing waveform followed by a second phase that can include a square wave or descending waveform of opposite polarity to the first phase.

Without wishing to be bound by theory, a waveform administered to the heart typically produces an effective voltage at various points in the heart. The shape of the waveform produced by the effective voltage may be different from the initial applied waveform at the point in the circuit where it is administered. The waveform shape of the effective voltage may be caused by inherent electrical properties of the heart such as resistance, capacitance and inductance. For example, the effective voltage of a biphasic shock in the heart may be modeled after a simple resistor-capacitor ("RC") circuit, in which the voltage across the RC circuit is believed to be related to the transmembrane voltage. For the truncated increasing exponential and ascending ramp first phase, the peak voltage across the RC circuit occurs at the very end of the waveform. Just before and after the peak voltage for the truncated exponential waveform, the voltage across the RC circuit is not changing very rapidly. Therefore, the voltage is near the peak voltage for some period of time. It is believed that a first ascending phase waveform that exceeds a certain effective voltage across the RC circuit for a certain period of time may facilitate efficient defibrillation.

Accordingly, biphasic waveforms having a first phase that exceeds a certain voltage for a period of time may be used. In certain embodiments, the first ascending phase maintains an effective voltage greater than about 50% to about 80% of the peak voltage for a duration greater than about 0.5 to about 1.0 ms. The ascending first phase can be an ascending ramp waveform. If an ascending ramp first phase were immediately followed by a second phase of opposite polarity, the second phase would immediately start removing voltage from the RC circuit, decreasing the time period of high voltage across the RC circuit. To avoid the immediate removal of voltage from the RC circuit, the first phase can be followed by an interval in which no shock is given, for example, lasting from about 1 to about 5 ms. The interval in which no shock is given may allow a higher voltage to be present for the interval across the RC circuit. Biphasic waveforms for maintaining a voltage for a certain period of time may include a 5 to 15 ms ascending first phase followed by a 2 ms interval in which no shock is given followed by a 1 to 5 ms second phase.

FIG. 3a illustrates a biphasic waveform in which there is no delay between the first ascending phase and the second phase having an opposite polarity. The top half of FIG. 3a is the administered current, and the bottom half of FIG. 3a is the resulting effective voltage. The negative second phase of the biphasic waveform, which begins at about 0.01 seconds as shown, drives down the effective voltage and returns to baseline. As a result, the effective voltage decreases rapidly after 0.01 seconds. In contrast, FIG. 3b illustrates a biphasic waveform in which there is a delay between the first and second phases. The top half of FIG. 3b is the administered current, and the bottom half of FIG. 3b is the resulting effective voltage. As can be seen by FIG. 3b, as a result of the delayed second phase, which begins at about 0.015 seconds, the effective voltage is maintained for a longer period of time during the delay period after the first phase.

In addition, the shape of the ascending first phase may be altered towards the end of the first phase to maintain effective voltage. For example, the first phase can have an ascending ramp followed by a square wave lasting 1 to 3 ms in which the voltage of the square wave is essentially equal to the peak of the ascending waveform. Alternatively, an exponentially increasing first waveform could be used that begins either at 0 volts or at some higher voltage such that the waveform would maintain a higher voltage towards the end of the first phase. An ascending waveform followed by a square wave or an increasing exponential waveform could either be followed immediately be the second phase of the biphasic waveform or followed by a short interval, for example 1 to 2 ms, and then by the second phase.

Drug Therapies.

In certain embodiments, various treatment techniques for reducing discomfort and/or the defibrillation threshold can be combined with administering a therapeutic drug. For example, a shock pulse sequence and/or shock timing for reducing the blood in the atria at the time of defibrillation can be combined with the administration of one or more therapeutic drugs. A therapeutic drug can be administered at a time and in an amount effective to decrease the strength of the defibrillation shock required to treat fibrillation. For example, the drug can be administered between about ten minutes prior to the defibrillation shock to contemporaneous with the defibrillation shock. The drug can be selected from the group consisting of a calcium channel blocker, a calmodulin blocker, a calmodulin kinase inhibitor, and an antiarrhythmic drug.

The therapeutic drug can include, but is not limited to, a calcium channel blocker, a calmodulin blocker, a calmodulin kinase inhibitor and an antiarrhythmic drug. The calcium channel blocker can include amiodarone, bepridil, D600, diltiazem, felodipine, flunarizine, israpine, nicardipine, nifedipine, nimodipine and verapamil. The antiarrhythmic drug can include adenosine, aprindine, doxorubicin, ryanodine, etlimozin, dofetilide and ibutilide. The calmodulin block can be a calmodulin kinase inhibitor. The therapeutic electric shock can be not greater than 34 joules. The calcium channel blocker can be administered in an amount effective to reduce the defibrillation threshold shock in the subject by at least 10% as compared to a normal defibrillation threshold shock. The defibrillation threshold shock can be reduced by at least 10% in leading edge voltage and by at least 20% in energy. The calcium channel blocker can be administered in an amount effective to inhibit a delayed after depolarization caused by the shock in the absence of the calcium channel blocker. See co-pending, co-owned application Ser. No. 10/071,269, the disclosure of which is hereby incorporated by reference in its entirety. The drugs can be administered in connection with a series of shocks including the shock sequences described herein. In certain embodiments, shock pulses and drug therapy may be automatically delivered as needed through a cardiac device, and may be administered externally or by an implantable device controlled by the patient, healthcare provider, or the defibrillation device. The drug therapy may be administered using techniques known to those of skill in the art including injection, oral dosages, or implantable devices. The drug may be administered locally or systemically. Drug delivery systems known to those of skill in the art may be used and are discussed herein.

Electrode Placement.

Systems for administering defibrillation shocks include electrodes placed in the cardiac region for administering therapeutic electric shocks. Shocks may be administered between electrode pairs or between three or more electrodes to defibrillate the heart. Examples of such placements include those disclosed in co-pending, co-owned application Ser. Nos. 10/087,340, 09/827,535 (which claims the benefit of U.S. provisional application Ser. No. 60/196,722, filed Apr. 13, 2000), the disclosures of which are hereby incorporated by reference in their entirety. Certain electrode placements, electrode pairs, and shock sequences administered between electrode pairs may reduce the discomfort experienced by a patient and/or reduce the defibrillation threshold.

Figure 4:
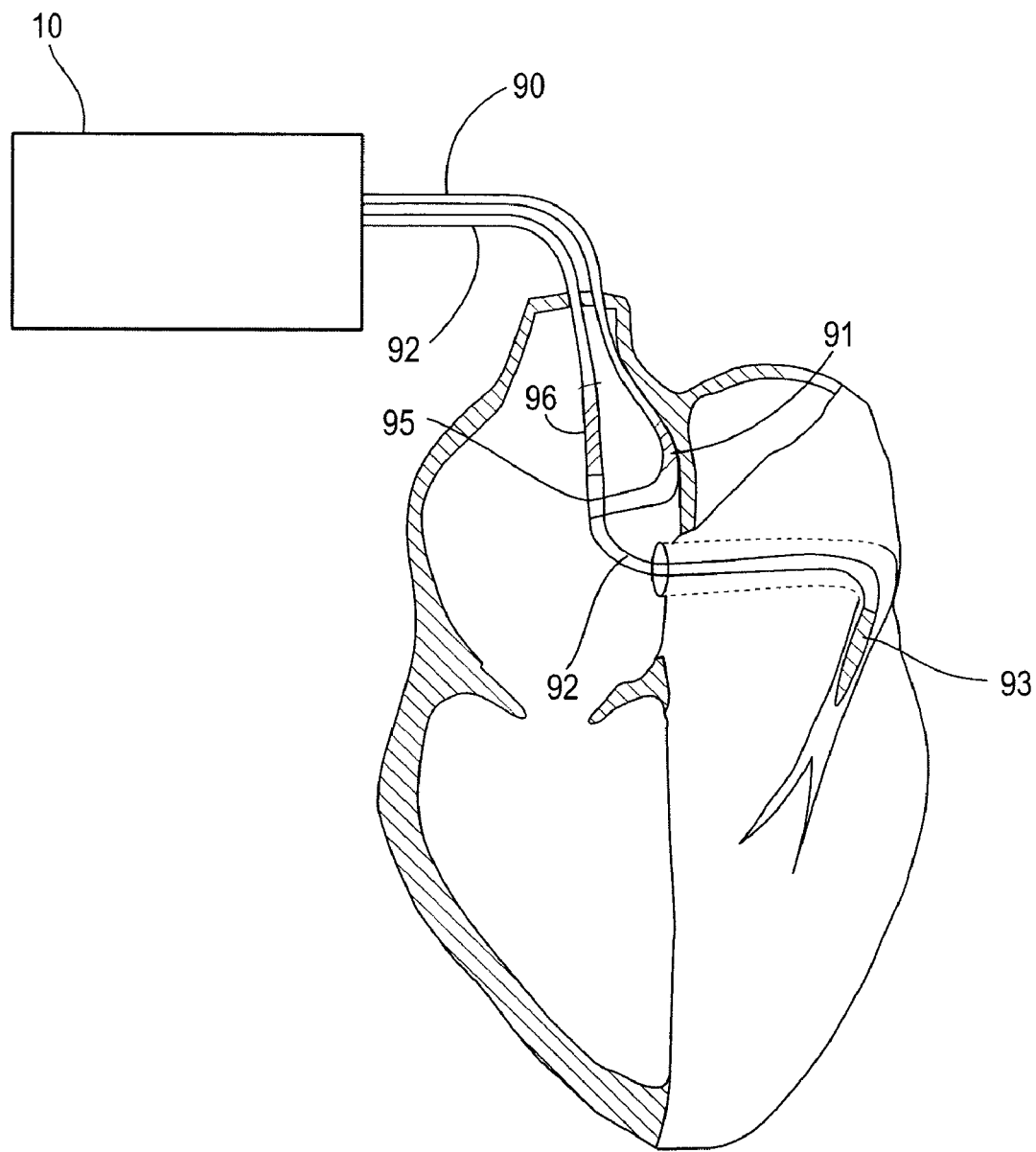
FIG. 4 is a schematic illustration of an implantable apparatus with exemplary electrode placements according to embodiments of the present invention.

FIG. 4, reproduced from application Ser. No. 10/087,340, illustrates an embodiment of an implantable system of the present invention and an exemplary electrode configuration carried by transveneous catheters. FIG. 4 is an example illustrating two spaced apart electrodes that form an potential gradient field and a third electrode placed in the gradient field. Other configurations of one or a plurality of electrodes can be used.

Referring to FIG. 4, the catheter 90 carrying the atrial septum electrode 91 is fixed to the catheter 92 carrying coronary sinus electrode 93 to form a catheter assembly and facilitate the holding of the atrial septum electrode against the atrial septum. Catheter 92 also carries atrial electrode 96. The system includes a defibrillator 10, which may incorporate features such as described in connection with defibrillator 10 as set forth herein. A connecting member 95, typically located at the distal end portion of the first catheter and connected to the intermediate portion of the second catheter, is included for interconnecting the two catheters. The atrial electrode 96 and the coronary sinus electrode 93 define an potential gradient field. Such a configuration or assembly, in addition to being suitable for carrying out the present invention has a variety of different applications.

A defibrillation shock can be delivered between the coronary sinus electrode 93 and the atrial electrode 96 electrode sequentially with a defibrillation shock between the atrial electrode 96 and the atrial septum electrode. The two defibrillation shocks together may defibrillate the heart more efficiently and/or with less discomfort to a patient than a single shock. Other configurations and shock sequences may be used. Preferred shock configurations and shock sequences include those discussed in application Ser. No. 10/087,340.

The defibrillation pulses may be delivered simultaneously or sequentially. The second defibrillation pulse may be delivered within 500 ms of the first defibrillation pulse. Each of the first and second defibrillation pulses may be less than about 150 volts in magnitude. In some embodiments, each of the defibrillation pulses are less than about four Joules in magnitude.

EMBODIMENTS

Figure 5:
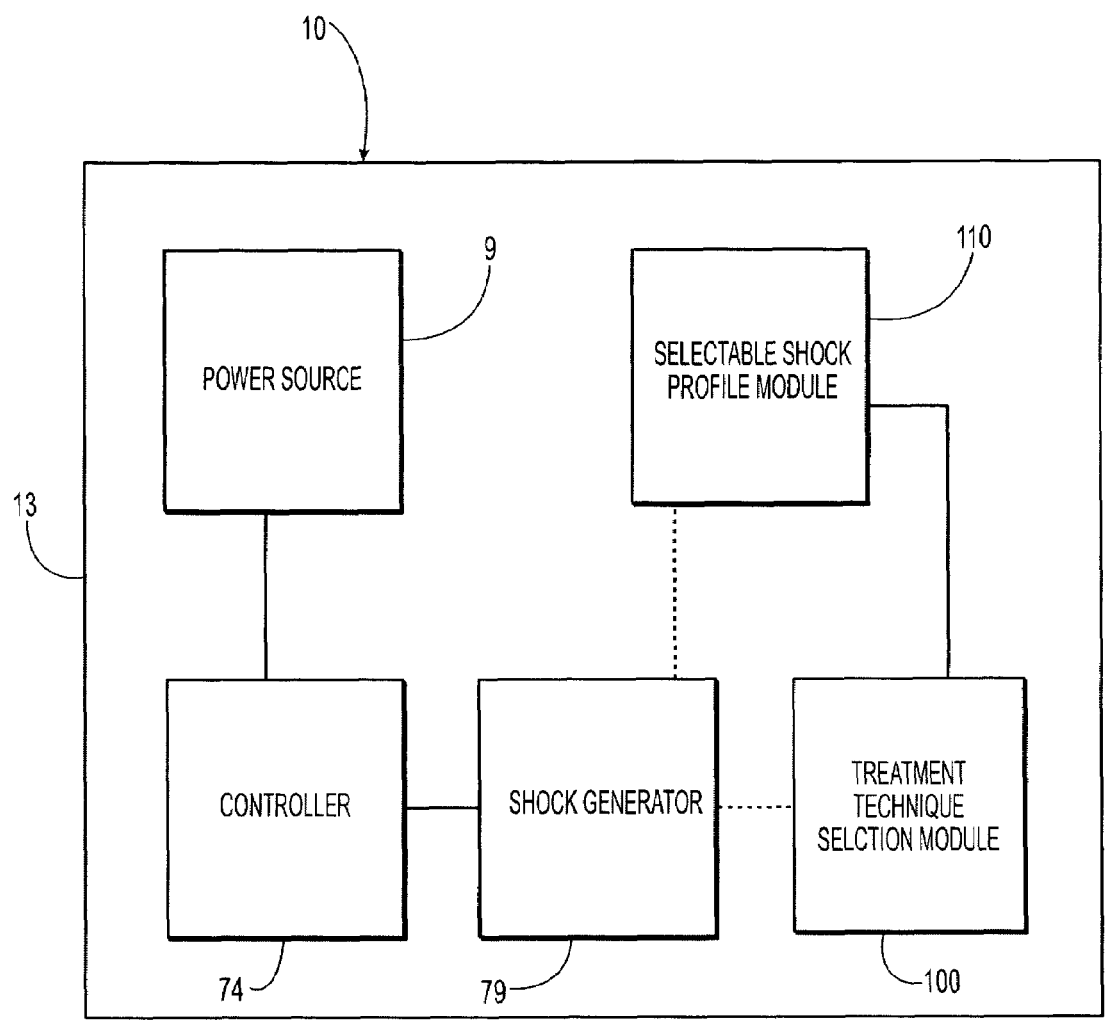
FIG. 5 is a schematic illustration of operational circuitry according to embodiments of the present invention.

Referring to FIG. 5, an exemplary atrial defibrillator 10 is shown. The atrial defibrillator 10 includes an implantable housing 13, a power source 9 held in the housing 13, and a controller 74 held in the housing 13 and operatively associated with the power source 9. A shock generator 79 is held in the housing 13 and operatively associated with the power source 9 and the controller 74. The shock generator 79 is configured to deliver one shock profile or a plurality of different selectable or predetermined shock profiles. A treatment technique selection module 100 may be operatively associated with the controller 74 for automatically selecting one or more predetermined treatment techniques for administering a defibrillation shock that reduces discomfort and/or the defibrillation threshold. Alternatively, the selection shock profile module 110 may be preprogrammed (such as by a clinician) to administer two or more patient-specific combined treatment techniques.

Figure 6:
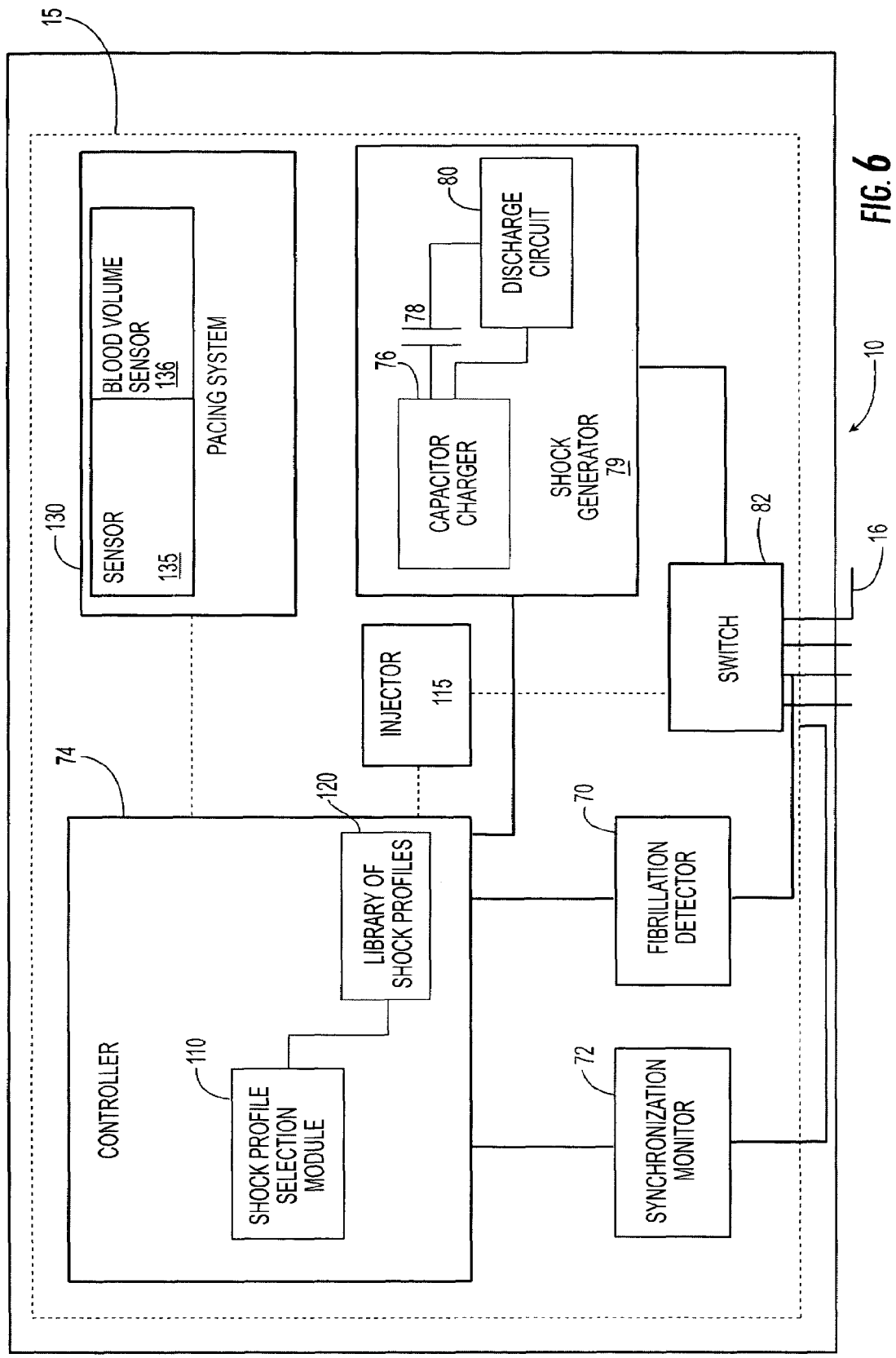
FIG. 6 is a schematic illustration of operational circuitry according to embodiments of the present invention.

FIG. 6 illustrates one example of an atrial defibrillator 10 held in implantable housing 13 and containing an electronic circuit 15 for generating, controlling and outputting defined shock profiles. The circuit 15 can include a controller 74, a shock profile selection module 110, a library of shock profiles 120, a synchronization monitor 72, a fibrillation detector 70, a sensor 135, a pacing system 130, a shock generator 79, discharge circuit 80, a capacitor charger 76, a storage capacitor 78, a switch 82 attached to leads 16, and one or more amplifiers (not shown) for amplifying sensed cardiac signals.

Cardiac signals are analyzed by an atrial and/or ventricular fibrillation detector 70 which determines if atrial fibrillation (or other types of cardiac arrhythmias, depending on the specific treatment for which the device is configured) is present. The detector 70 may be one of several known to those skilled in the art. The sensed signal may be provided by an electrode. It will be appreciated by those of skill in the art that the sensing electrode may also be a plurality of sensing electrodes with a plurality of signals, such as configurations of electrodes 91, 93, and 96 shown in FIG. 4, and may also be electrodes positioned in alternate cardiac areas as is known in the art. In this situation, the input line to the detector may be a plurality of leads 16 which, if providing only sensing, will provide an input to the detector. Leads 16 may also provide electrical signals to the cardiac electrodes.

Thus, in certain embodiments, the implantable system for the defibrillation of the atria of a patient's heart comprises: (a) one or more electrodes or electrode pairs configured for delivering a defibrillation pulse, for example, along a desired current pathway(s) in the heart; and (b) a shock generator operatively associated with the atrial defibrillation electrodes, such as the electrodes 91, 93, and 96 depicted in FIG. 4, for delivering the defibrillation pulse. Electrodes or electrode pairs may be placed in a variety of different locations. A single electrode may participate in more than one electrode pair, so that, for example, two current pathways are achieved through three defibrillation electrodes. Additional electrodes may be tied together to one member of an electrode pair to provide a single pole, if so desired, and additional electrodes may be provided for following a shock with additional shocks. One example of such a system is shown in U.S. Pat. No. 6,122,553.

Ventricular sensing for timing the shocks for atrial defibrillation may be performed from electrodes placed in the right and/or left ventricles.

The electronic circuit 15 can also include a cardiac cycle monitor ("synchronization monitor 72") for providing synchronization information to the controller 74. The synchronization can be provided by sensing cardiac activity in the right ventricle, but may also include other sensing electrodes which can be combined with the defibrillation electrodes or employed separately to provide additional assurance that defibrillation shock pulses are not delivered during sensitive portions of the cardiac cycle so as to reduce the possibility of inducing ventricular fibrillation.

One or more of the defibrillation electrodes may be configured to sense cardiac cycles from electrical signals from the heart, or may have smaller sensing electrodes placed adjacent thereto and thereby provide input to the electronics package as well as provide a predetermined stimulation shock output to predetermined cardiac areas as directed by the controller 74. As also shown in FIG. 6, the electronic circuit 15 may also include a pacing system 130 for reading and monitoring cardiac cycles from the electrical signals from the heart sensed by the electrodes. The pacing system 130 may include one or more sensors 135 for sensing various cardiac signals, including cardiac rhythms. An example of a sensor is a blood volume sensor 136. The blood volume sensor 136 may detect the volume of blood in a particular area such as the atria by monitoring cardiac electrical signals, blood pressure, or heart beat.

Still referring to FIG. 6, upon a signal from the detector 70 that indicates the existence of an arrhythmia, the controller 74 signals the shock generator 79 to generate a shock having a particular selected shock profile. The shock generator 79 may include a capacitor charging circuit 76 which then charges the storage capacitor 78 to a predetermined voltage, typically from a power source such as a battery source. The storage capacitor 78 is typically 20 to 400 microfarads in size, and may be a single capacitor or a capacitor network (further, as discussed below, separate pulses can be driven by the same or different capacitors). The discharge of the capacitor is controlled by the controller 74 and/or a discharge circuit 80. The controller 74, which may also consider information from the synchronization monitor 72, typically allows or directs the desired shock profile to be relayed to either a discharge circuit 80 for further processing (i.e., to further shape the waveform signal, time the pulse or pulses, etc.) or directly to an output switch such as switch 82. The controller 74 may also control the desired or proper selection of the predetermined defibrillation electrode pair(s), where multiple defibrillation electrodes are used, to direct the switch 82 to electrically activate a desired electrode pair to align the predetermined electric shock pulse pathway through which the shock pulse is provided. As an alternative to a defibrillation detector 70, the defibrillation shock profiles may be triggered by an external signal administered by a physician, with the physician monitoring the patient for the appropriate time of administration. A plurality of predetermined defibrillation shock profiles may be preprogrammed into a library of predetermined shock profiles 120 for selection by the shock profile selection module 110. Thus, the controller 74 includes or is operably associated with a library of selectable predetermined shock profiles 120. The library of selectable predetermined shock profiles 120 includes specifications and/or instructions that define shocks having various shock profiles. The shock profile is selected by the shock profile selection module 110 and communicated to the discharge circuit 80 for use in processing the shock pulse(s) to the desired shock profile specification.

It will be appreciated by those of skill in the art that the capacitor 78 can be two or more separately charged capacitors (or bank of parallel capacitors) on separate lines to provide two separate and sequential shock pulses as controlled by the controller 74 and/or the discharge circuit 80. However, it is preferred that the capacitor 78 be a relatively large capacitor for insuring sufficient charge and decay period (i.e., long time constant and low tilt) to provide sufficient energy for shock pulses. For example, a capacitor with capacitance in the range of 200-1000 μf or more, having an associated time constant in the range of 30 ms, would typically be charged to approximately 100-200 volts and would deliver a V(peak) in a typical first waveform of about 50-100 volts leading edge. If additional shocks greater than two are administered during an episodic delivery, then a larger capacitor may be employed. In the alternative wherein the electronic package employs a circuit to further shape the waveform, the capacitor may be charged to a higher voltage range (such as around 200 volts).

In one embodiment of the invention, the shock generator 79 includes a single capacitor 78, and the controller 74 includes a switch (e.g., a crosspoint switch) operatively associated with that capacitor. The controller 74 is configured to provide a shock profile consisting of a biphasic pulse (i.e., a first phase of a pulse of a predetermined polarity followed by a second phase of a pulse of reversed polarity), which consists of a first atrial defibrillation pulse and a biphasic pulse as a second atrial defibrillation pulse. Monophasic and triphasic pulses may also be used.

In operation, the controller 74 delivers a preselected electrical pulse to predetermined electrode pairs through a switch 82, which is preferably programmable. The shock generator 79 (including a capacitor charger 76, capacitor 78, and discharge circuit 80), controller 74, and switch 82 thus work in concert to produce and deliver a shock having a particular shock profile. Therefore, it will be appreciated that, in operation, in response to an input from the atrial fibrillation detector 70, or a shock profile selection module 110, the controller 74 controls the pulse or shock generator 79 to synchronize the delivery of the timed pulse output to the proper electrode or electrode pair in accordance with the cardiac cycle information received from the synchronization monitor 72 and the specific electrode configuration employed by or selected by the device. Further, when employing a biphasic waveform, it will be appreciated by those of skill in the art that the pulse or shock generator 79 can also include a crosspoint switch to switch the polarity of the electrode pair for delivery of the second (inverted or negative) waveform phase. The electronic circuit 15 may also include a receiver/transmitter coupled to the internal controller 74 for communicating with an external controller. Thus, the pulse regimen could be altered by external input to the controller to alter for example, the waveform, the voltage, the electrode coupling, or even to retrieve data monitoring data received and stored in memory about the number of atrial fibrillation episodes and the effectiveness of the shock level.

In one embodiment, the switch 82 is programmable (e.g., by remote control such as by a radio signal) to alter the coupling of the pulse generator to the atrial defibrillation electrodes. This feature is advantageously employed when multiple electrodes are implanted so that the electrode pairs that deliver the shocks may be changed to customize and/or optimize the technique for a particular patient.

In certain embodiments, the sensor 135 (FIG. 6) is an arrhythmia detector configured to determine if a cardiac arrhythmia is occurring and a blood volume sensor 136 to detect the ventricular cardiac cycle from electrical activity sensed from the heart of a subject. The sensor functions of the sensor 135 and the blood volume sensor 136 may be controlled by a single sensor or multiple components. The controller 74 can be configured to communicate instructions to the shock generator 79 to deliver a defibrillation shock to the atria of the heart at a time during the ventricular cardiac cycle at which atrial blood volume is reduced.

In some embodiments, an injector 115 can be operatively associated with the controller 74 to administer a therapeutic drug to the subject, as discussed above. A calcium control blocker, calmodulin blocker, calmodulin kinase inhibitor, antiarrhythmic, or other therapeutic drug may be placed into the injector 115 when the device is produced. The drug may also be placed in a wire or catheter that can be connected to a system outside of a subject's body and/or an implantable device. A catheter may be used to inject the calcium channel blocker or drug directly into the bloodstream rather than through the device. The catheters may also be used to place electrodes in the cardiac region. Other drug delivery systems known to those of skill in the art may be used, including osmotic pumps and drug reservoirs.

The controller 74 can be configured to communicate instructions to the shock generator 79 to deliver various shock profiles, including waveforms, and shock sequences at desired timed intervals to desired electrode(s). The shock generator 79 can deliver shocks to various electrode placement configurations. For example, the controller 74 can be configured to communicate instruction to deliver a preparatory shock to the atria of the heart followed by the defibrillation shock to the atria at a time sufficient to allow contraction of the atria. The preparatory shock can have a strength less than the defibrillation shock. The controller 74 can also be configured to release the therapeutic drug locally with or proximate to the administration of the defibrillation electric shock so that the strength of the shock is decreased as compared to the shock required to treat the arrhythmia in the absence of administration of the therapeutic drug. The therapeutic drug is typically released about 0.5-1 seconds to about 5 minutes prior to the defibrillation shock. The sensor 135 can detect atrial cardiac activity and/or ventricular cardiac activity and can be an atrial arrhythmia detector and/or a ventricular arrhythmia detector.

While the present invention is illustrated in certain of the figures, for example, with reference to particular divisions of programs, functions and memories, the present invention should not be construed as limited to such logical divisions. Thus, the present invention should not be construed as limited to the configuration of operation as shown in FIGS. 5 and 6 but is intended to encompass any configuration capable of carrying out the operations described herein.

FIG. 67 is a block diagram of exemplary embodiments of data processing systems that illustrates systems, methods, and computer program products in accordance with embodiments of the present invention. The data processing system 305 may be implemented externally or internally with respect to the patient. The shock generation system 320 may be implanted in the patient and the sensor system 325 may include sensors either implanted in the patient along with the shock generation system or situated at internal or external regions of the patient.

The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

Figure 7:
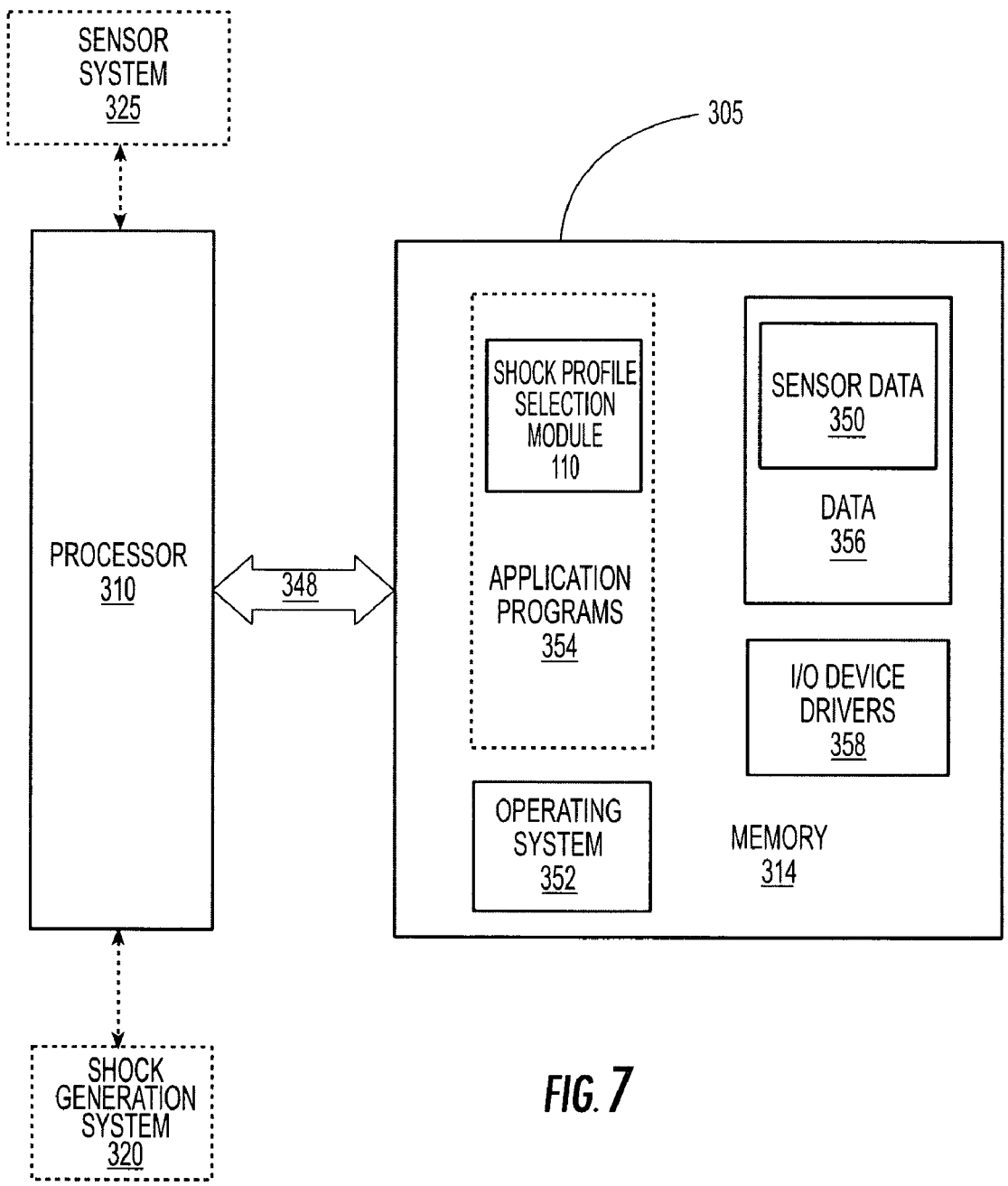
FIG. 7 is a schematic illustration of alternative embodiments of operational circuitry and/or computer program modules suitable for carrying out operations of embodiments of the present invention.

As shown in FIG. 7, the memory 314 may include several categories of software and data used in the data processing system 305: the operating system 352; the application programs 354; the input/output (I/O) device drivers 358 and the data 356. The data 356 may include sensor data 350 which may be obtained from a sensor system 325 that senses electrical signals from the patient such as the atrial in situ an dynamically real time defibrillation electrical complex. The shock profile selection module 110 may communicate the desired shock profiles to a shock generation system 320 for delivery to a patient.

As will be appreciated by those of skill in the art, the operating system 352 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, LabView or proprietary operating systems. The I/O device drivers 358 typically include software routines accessed through the operating system 352 by the application programs 354 to communicate with devices such as I/O data port(s), data storage 356 and certain memory 314 components and/or the shock generation system 320 and sensor system 325. The application programs 354 are illustrative of the programs that implement the various features of the data processing system 305 and preferably include at least one application which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the shock profile selection module 110 being an application program in FIG. 6, as will be appreciated by those of skill in the art, other configurations may also be utilized while still benefiting from the teachings of the present invention. For example, the shock profile selection module 110 may also be incorporated into the operating system 352, the I/O device drivers 358 or other such logical division of the data processing system 305. Thus, the present invention should not be construed as limited to the configuration of FIG. 7, which is intended to encompass any configuration capable of carrying out the operations described herein.

The I/O data port can be used to transfer information between the data processing system 305 and the shock generation system 320 and sensor measurement system 325 or another computer system or a network (e.g., the Internet) or to other devices controlled by the processor. These components may be conventional components such as those used in many conventional data processing systems that may be configured in accordance with the present invention to operate as described herein.

Although the system has been primarily described above as an implantable system, it will be appreciated by those of ordinary skill in the art that the invention could also be incorporated into an external system which employs catheters to position the electrodes within a patient's heart or other desired configuration.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for reducing discomfort associated with atrial defibrillation comprising:
    delivering a preparatory shock to the atria of the heart of a subject experiencing arrhythmia to contract the atria to reduce a blood volume in the atria for a time period subsequent to the shock; and then
    delivering an atrial defibrillation shock to the atria of the heart after the preparatory shock during contraction of the atria, wherein the preparatory shock has a strength less than the defibrillation shock.

2. The method according to claim 1, further comprising:
    administering a therapeutic drug selected from the group consisting of a calcium channel blocker, a calmodulin blocker, a calmodulin kinase inhibitor and an antiarrhythmic drug to the subject.

3. The method according to claim 1, wherein the time between the preparatory shock and the defibrillation shock is between about 50 and about 500 ms.

4. The method according to claim 1, wherein the voltage of the preparatory shock is between about 5 and 100V and the voltage of the defibrillation shock is between about 10 and about 200V.

5. The method according to claim 1, wherein the defibrillation shock is less than about 34 joules.

6. The method according to claim 1, further comprising:
    positioning first and second defibrillation electrodes in operable association with the heart of a subject, the first and second defibrillation electrodes defining a potential gradient field in the heart, the potential gradient field including a region of the heart to be defibrillated;
    positioning a third electrode in the gradient field between the first and second electrodes: and
    wherein the defibrillation shock further comprises: sequentially delivering (a) a first defibrillation shock between the first and third electrode and (b) a second defibrillation shock between the second and third electrodes: with the first and second defibrillation shocks together effective to defibrillate the heart.

7. A method according to claim 6, wherein the first and second defibrillation shocks are delivered simultaneously.

8. A method according to claim 6, wherein the first and second defibrillation shocks are delivered sequentially.

9. A method according to claim 6, wherein each of the first and second defibrillation shocks are less than about four Joules in magnitude.

10. The method according to claim 1, further comprising:
    determining the fibrillation cycle length; and after delivering the defibrillation shock, delivering a second defibrillation shock to the heart, wherein the second defibrillation shock is spaced apart from the defibrillation shock by about 80% to about 90% of the time of the fibrillation cycle length.

11. The method according to claim 10, further comprising: delivering a third defibrillation shock spaced apart from the second defibrillation shock by about the time of the fibrillation cycle length.

12. The method according to claim 1, further comprising detecting blood pressure to determine when the atrial blood volume is reduced.

* * * * *

UNITED STATES PATENT AND TRADEMARK OFFICE
CERTIFICATE OF CORRECTION

PATENT NO.         : 7,522,958 B2                                   Page 1 of 1
APPLICATION NO.    : 10/388211
DATED              : April 21, 2009
INVENTOR(S)        : Ideker et al.

It is certified that error appears in the above-identified patent and that said Letters Patent is hereby corrected as shown below:

<u>Title Page, (74) Attorney, Agent or Firm:</u>

Please correct "Myers Sigel Sibley & Sajovec"
    to read -- Myers Bigel Sibley & Sajovec --

Signed and Sealed this

Twenty-first Day of July, 2009

JOHN DOLL
*Acting Director of the United States Patent and Trademark Office*